United States Patent [19]

Waldvogel et al.

[11] Patent Number: 5,670,648
[45] Date of Patent: Sep. 23, 1997

[54] INTERMEDIATES FOR PYRAZOLYL ACETIC ACID DERIVATIVES

[75] Inventors: Erwin Waldvogel, Aesch; Eugen Eichenberger, Anwil, both of Switzerland

[73] Assignee: Sandoz Ltd., Basel, Switzerland

[21] Appl. No.: 742,549

[22] Filed: Nov. 1, 1996

Related U.S. Application Data

[63] Continuation of Ser. No. 523,729, Sep. 5, 1995, abandoned.
[51] Int. Cl.$^6$ ................................................. C07D 231/18
[52] U.S. Cl. .............................................. 548/370.4
[58] Field of Search ................................... 548/370.4

[56] References Cited

FOREIGN PATENT DOCUMENTS 433899  12/1990  European Pat. Off. .
9417060  8/1994  WIPO .

OTHER PUBLICATIONS

Tetrahedron Letters, No. 19, Apr. 1971, pp. 1591–1592.

*Primary Examiner*—Robert W. Ramsuer
*Attorney, Agent, or Firm*—Lynn Marcus-Wyner

[57] ABSTRACT

The invention discloses a novel process for the preparation of a compound of formula II

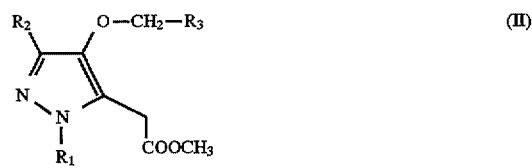

wherein
$R_1$ is $C_{1-5}$alkyl,
$R_2$ is hydrogen or $C_{1-5}$alkyl, and
$R_3$ is optionally substituted phenyl,
comprising the reaction of a 4-hydroxypyrazole of formula III

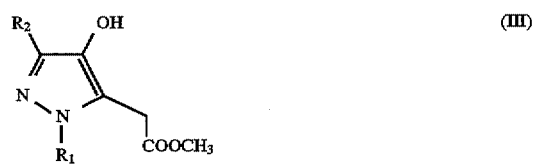

wherein $R_1$ and $R_2$ are as defined for formula II, with a benzylhalide of formula IV

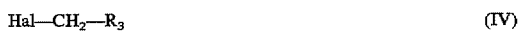

wherein Hal is halogen, preferably bromine or chlorine, and $R_3$ is as defined for formula II, in the presence of a base. The invention further comprises a novel process for the preparation of the 4-hydroxypyrazole of formula III. The compounds of formulae II and III are intermediates for highly effective systemic fungicides of the class of pyrazolyl acetic acid derivatives.

1 Claim, No Drawings

INTERMEDIATES FOR PYRAZOLYL ACETIC ACID DERIVATIVES

This is a continuation of application Ser. No. 08/523,729, filed on Sep. 5, 1995 abandoned.

The present invention relates to a novel process for the preparation of intermediates for pyrazolyl acetic acid derivatives, and to novel intermediates prepared for conducting said process.

Pyrazolyl acetic acid derivatives as obtainable from the intermediates preparable by the process of present invention are known in literature as highly effective systemic fungicides against phytotoxic fungi being useful for protection of plants cultivated in agriculture and horticulture. Such pyrazolyl acetic acid derivatives are known from EP-A-433899, WO 94/17060 and JP-05/201980. However, the described process for preparation involves multiple steps and overall has a low yield. For industrial production there is still a strong need for a simplified and improved process and synthesis route leading to higher yields.

It has now been found that the compounds of formula I

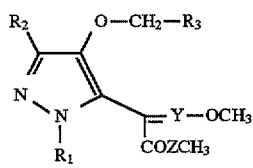

wherein $R_1$ is $C_{1-5}$alkyl, $R_2$ is hydrogen or $C_{1-5}$alkyl, $R_3$ is optionally substituted phenyl, Y is nitrogen or CH, and Z is oxygen or NH, may be obtained in good yields according to the novel process of this invention.

The radicals as defined under $R_3$ are not critical for the present process. They encompass aromatic groups in general with a unlimited variety of substitution patterns, which of course are only limited where incompatible with intermediates or reaction conditions of the new process. Preferably, the definition of $R_3$ is in accordance with the compounds disclosed in EP-A-433899, which definition is incorporated herein by reference. In a more preferred subgroup $R_3$ is phenyl optionally substituted by one to three radicals selected from halogen, $C_{1-4}$alkyl or $C_{1-4}$haloalkyl, wherein the preferred radicals are fluorine, chlorine, methyl, ethyl, isopropyl, fluoromethyl, chloromethyl or trifluoromethyl. Most preferred $R_3$ is dichlorophenyl. Methyl is preferred for $R_1$ and $R_2$.

Instead of the benzyl derivatives of formula I wherein $R_3$ is optionally substituted phenyl, the heteroaryloxy derivatives of WO 94/17060 may be obtained by the process of this invention, when suitable heteroaryl starting materials are employed in place of the benzyl compounds of formula IV and reacted with the compound of formula III, c.f. to formulae VII or VIII in Scheme 1 of WO 94/17060.

The key intermediates for preparing the fungicidal pyrazolyl acetic acid derivatives of formula I are the pyrazolyl acetic acid derivatives of formula II

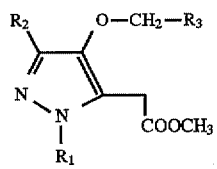

wherein $R_1$, $R_2$ and $R_3$ are as defined for formula I.

The compounds of formula I may be obtained from the key intermediates of formula II by methods known per se. These methods include a first step of activating the α-position of the acetic acid radical, and reacting the compounds of formula II with a hydroxymethylenating or an oxime forming agent, followed by a methylating step, forming the compounds of subformulae Ia and Ib, respectively. Optionally these compounds may further be converted to N-methylamides by a conventional trans-amidation reaction, e.g. to subformula Ic. The principle reaction routes are outlined in the following Scheme 1. The methods per se are known from EP-A433 899, JP-05/201980 and EP-A-499 823.

Scheme 1:

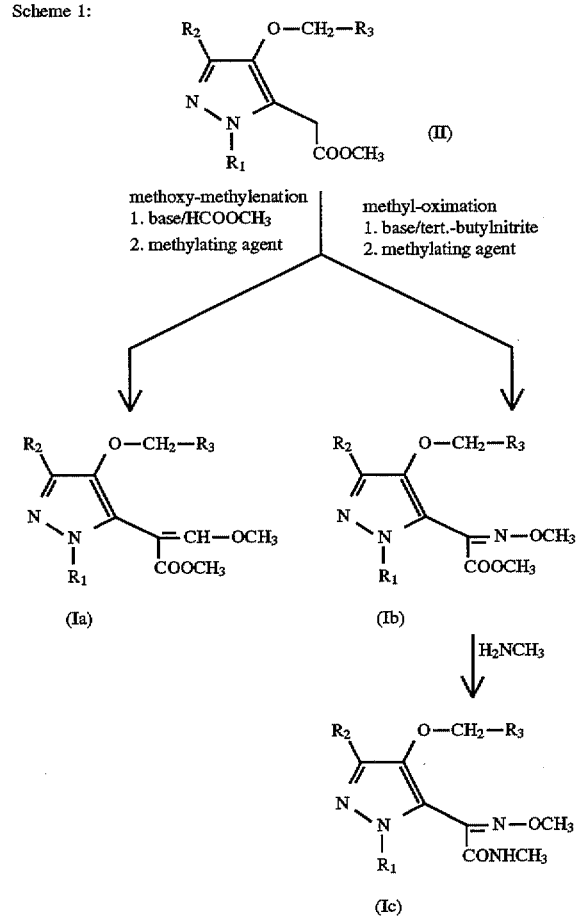

The methoxy-methylenation step (II→Ia) is carried out by reacting the intermediate of formula II with methyl formate and a base in the presence or absence of an inert solvent to give the hydroxy-methylenated form of compound II which may be isolated, if desired. This hydroxy-methylenated product is further methylated with a methylating agent. With advantage also the methylation step is carried out under basic conditions in the presence or absence of an inert solvent. The reactions may be carried out at a temperature in the range of about −78° C. to the boiling point of the solvent to be used, preferably 0° to 150° C. Inert solvents which may be used include aromatic hydrocarbons such as benzene, toluene, and the like; ethers such as diethyl ether, tetrahydrofuran, and the like; polar solvents such as dimethylformamide, dimethyl sulfoxide, and the like; or a mixture comprising two or more of them. Bases which may be used include alkaline metal hydroxides such as sodium hydroxide, and the like; alkaline metal hydrides such as sodium hydride, and the like; alkaline metal alcoholates such as sodium methylate, and the like; alkaline metal carbonates such as potassium carbonate and the like. Methylation reagents include methyl iodide, dimethyl sulfate, and the like. Alternatively, the conversion (II→Ia) may also be conducted by forming an α-ketoester first, e.g. by oxidation with selenium oxide or the like, and converting the α-ketoester into the compound of formula I with a Wittig reagent prepared from e.g. tripbenylphosphonium halide and methoxymethyl chloride. Appropriate reaction conditions for this alternative route of reaction (II→Ia) are known from EP-A-433899.

The methyl-oximation step (II→Ib) is carried out by reacting the intermediate of formula II with an alkylnitrite, e.g. tert. butylnitrite. With advantage the oximation step is carried out in the presence of a base and in the presence of an inert solvent. The reaction may be carried out at a temperature in the range of −78° C. to the boiling point of the solvent to be used, preferably between −50° C. and +30° C. Inert solvents, bases and methylating agents may be selected from the groups given for the methoxy-methylenation reaction (II→Ia). Alternatively the conversion (II→Ib) may also be effected by oxidising the compounds of formula II with a suitable oxidising agent to a α-keto-ester and then reacting this ester with methoxy-lamine hydrochloride, or with hydroxylamine hydrochloride and subsequent methylation with methyliodide or dimethylsulfat. Optionally the ester-type compound of subformulae Ia and Ib may be transformed into the amides (Z is NH) by conventional trans-amidation, e.g. by treating the ester with methylamine.

According to the present invention the compounds of formula II

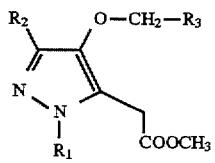

wherein $R_1$, $R_2$ and $R_3$ are as defined for formula I are prepared by a process comprising the reaction of a 4-hydroxypyrazole of formula III

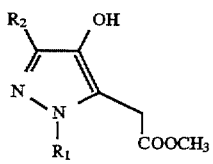

wherein $R_1$ and $R_2$ are as defined for formula I, with a benzylhalide of formula IV

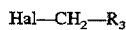

wherein Hal is halogen, preferably bromine or chlorine, and $R_3$ is as defined for formula I, in the presence of a base.

The etherification reaction step (III+IV→II) is carried out in the presence of base being capable of neutralizing the hydrogen halide produced by the etherification reaction. Suitable bases are organic or inorganic bases like tertiary amines or alkaline bases like potassium or sodium carbonates or bicarbonates, or sodium hydride. With advantage this step is carried out in an inert solvent such as tetrahydrofuran, diethylether, diisopropylether, dimethylformamide, N-methylpyrrolidone, acetonitrile, dimethylsulfoxide, or acetone. Reaction temperatures are not critical, but would preferably be between 0° C. and the boiling point of the mixture, e.g. at more temperature or at +50° C.

Most of the starting material compounds of formula III are novel. The compounds of formula III wherein $R_1$ is hydrogen or methyl and $R_2$ is methyl are known from WO 94/17060. The novel compounds of formula III have especially been developed for the process of present invention and thus constitute an aspect of present invention. The methylhalides of formula IV are known or can be prepared according to known methods. Many of the compounds of formula IV are commercially available.

According to the main aspect of present invention the 4-hydroxy pyrazoles of formula III may be obtained by an intramolecular cyclization reaction of a compound of formula V

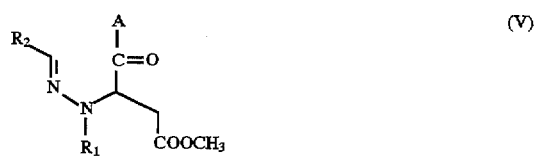

wherein $R_1$ and $R_2$ are as defined for formula I and A is a leaving group, at a temperature between +50° C. and +200° C., preferably between +50° C. and +180° C. The cyclization reaction is advantageously carried out without any solvent, i.e. by heating the compound of formula V, or it is carried out in the presence of an aprotic solvent such as acetonitrile, N-methylpyrrolidon, N,N-dimethylacetamide, dimethylformamide, xylene, dichlorobenzene or the like. If low boiling solvents are used, the reaction is preferably carried out in a pressure vessel. The reaction rate is substantially lower when non-polar solvents are used. The leaving group is preferably a radical derived from the acyloxy group of mixed acid anhydrides or from aromatic alcohols, i.e. optionally substituted phenols or thiophenols. Particularly suitable leaving groups A may be selected from α- and β-naphtyloxy, phenylthio, 4-methylphenylthio, 4-methoxyphenylthio, 4-chlorophenylthio, 4-ethoxycarbonyl phenoxy, 4-cyanophenoxy, 4-benzoylphenoxy, 4-nitrophenoxy, phenoxy, acetoxy, trifluoroacetoxy, methylsulfonyloxy, trifluoromethlysulfonyloxy, phenylsulfonyloxy, toluylsulfonyloxy and the like.

The compounds of formula V may be obtained from condensation of an aspartic acid derivative of formula VI

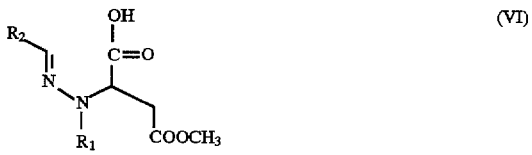

wherein $R_1$ and $R_2$ are as defined for formula I, with an acyloxylating agent or an optionally substituted phenol or thiophenol of formula VII

wherein A is as defined for formula V. This acyloxylating or esterification reaction may be conducted under standard conditions for acyloxylations and esterifications. For the esterifications it is however preferred to synthezise these compounds of formula V from the acids of formula VI by treating the free acid with ethyl- or isobutyl-chloroformate in the presence of a base e.g. triethylamine first, and then reacting the obtained reaction mixture with the phenol or thiophenol of formula VII. The reaction is advantageously carried out in an inert solvent, e.g. ethers such as tetrahydrofuran, diethylether, dioxane and the like, or halogenated hydrocarbons such as methylene chloride, chloroform, CCl$_4$ or trichloroethane. The reaction is preferably carried out with cooling at temperatures in the range of about −78° C. to +30° C., preferably −30° C. to −10° C.

The aspartic acid derivative of formula VI may be obtained by reacting maleic acid monomethyl ester of formula VIII

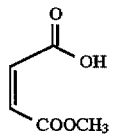
(VIII)

in the presence of a tertiary amine like triethylamine with a hydrazine derivative of formula IX

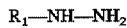
(IX)

wherein R$_1$ is as defined for formula I, and reacting the obtained intermediate product of formula X

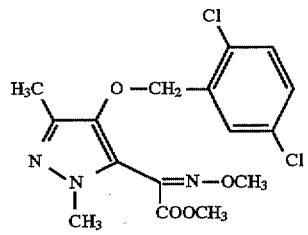

wherein R$_1$ is as defined for formula I, with an aldehyde of formula XI

(XI)

The above reaction (VIII→X→VI) may be conducted in a single vessel as a two-step-reaction without isolating the intermediate of formula X. However, if desired isolation will be possible in a manner known per se for isolation procedures. The single vessel reaction may be carried out in an inert solvent such as acetonitrile, toluene or an ether solvent such as tetrahydrofuran, diethylether or dioxane and the like. Reaction temperatures are not critical, but are advantageously in the range of −25° C. to the boiling point of the mixture, preferably between 0° C. and +30° C. Instead of the maleic acid mono methyl ester used as starting material of formula VIII, also the corresponding fumaric acid mono methyl ester may be employed.

The addition reaction of the hydrazine derivative of formula IX to the maleic monomethyl ester is very selective under two aspect: firstly, only the substituted nitrogen atom forms the link, and secondly the addition is directed only to the β-position of the ester group. Surprisingly high yields are obtained in this reaction step.

The starting material of formula VIII is known in the art, and may be obtained from maleic anhydride with methanol.

Likewise starting materials of formulae VII, IX and XI are known, and are in many cases also commercially available.

The preparation processes (V→II), (VI→V) and (VIII→X→VI) are novel and have especially been developed to prepare the starting material of formula II for the process of this invention. These processes also constitute further aspects of present invention. Also the intermediates of formulae V, VI, and X are novel and have been developed within the same inventive concept. These compounds as well represent another aspect of present invention.

The following examples illustrate present invention without limiting it.

EXAMPLES

Examples 1

Methyl α-[1,3-dimethyl-4-(2,5-dichlorobenzyloxy)-1H-pyrazol-5-yl]-β-methoxy-acrylate

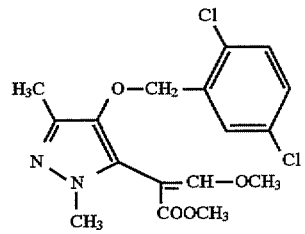

Methyl α-[1,3-dimethyl-4-(2,5-dichlorobenzyloxy)-1H-pyrazol-5-yl]-acetate

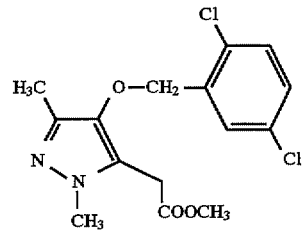

A mixture of 2 g of methyl α-(1,3-dimethyl-4-hydroxy-1H-pyrazol-5-yl)-acetate (10.85 mmoles), 2.33 g 2,5-dichlorobenzylchloride (11.9 mmoles), 3.75 g K$_2$CO$_3$ (27.1 mmoles), 180 mg KI (1.08 mmoles) and 100 ml acetone is stirred for 20 hours at +50° C. The reaction mixture is filtered and the filtrate is evaporated. The oily residue is purified by column chromatography on silica gel. Eluent: ethyl acetate/toluene 1:1. Yield: 2.68 g of methyl α-[1,3-dimethyl-4-(2,5-dichlorobenzyloxy)-1H-pyrazol-5-yl] acetate in the form of yellowish crystals (72%). mp: +72° C.

$^1$H-NMR (360 MHz in CHCl$_3$): 2.20 (s, CH$_3$); 3.59 (s, CH$_2$); 3.61 (s, CH$_3$N); 3.62 (s, CH$_3$O); 4.90 (s, CH$_2$O), 7.25 (dd, J$_1$=8 Hz, J$_2$=3 Hz, Ph-H); 7.32 (d, J=8 Hz, Ph-H); 7.56 (d, J=3 Hz, Ph-H). MS: M$^+$=342/344/346. IR (KBr): 1736 cm$^{-1}$ (COO).

b) A 2.5 l vessel is charged with 41.7 g sodium methanolate, 400 ml dimethylformamide and 1 ml methanol. In order to prevent foaming to this solution is added dropwise and at room temperature a solution of 192.5 g methyl α-[1,3-dimethyl-4-(2,5-dichlorobenzyloxy)-1H-pyrazol-5-yl-]-acetate and 450 ml methyl formate in 200 ml dimethylformamide. The reaction mixture is stirred for 4 hours at room temperature, then 76 g of dimethylsulfate is added and stirring continued over night. Evaporation of the solvents and partition of the remaining dark oil between ethyl acetate and water, and isolating the product from the organic phase gave 210 g red oil. Crystallisation of this oil in a mixture of ethyl acetate and hexane gave 158 g (82.3%) of methyl α-[1,3-dimethyl-4-(2,5-dichlorobenzyloxy)-1H-pyrazol-5-yl]-β-methoxy-acrylate in form of a slightly beige colored solid, mp. 94°–96° C.

Example 2

Methyl α-(1,3-dimethyl-4-hydroxy-1H-pyrazol-5-yl)-acetate

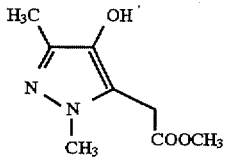

A solution of 17 g of methyl 4-(4-chlorophenylthio)-3-(2-ethylidene-1-methylhydrazino)-4oxo-butyrate in 170 ml 1-methyl-pyrrolidone is heated for 4 hours to +140° C. The solvent is evaporated completely and the residue purified by chromatography on silica gel. Eluent: ethyl acetate/toluene 3:1. Yield: 4.8 g of methyl α-(1,3-dimethyl-4-hydroxy-1H-pyrazol-5yl)-acetate in the form of yellowish crystals (50%). mp: 118°–119° C.

$^1$H-NMR (360 MHz in CDCl$_3$): 2.13 (s, CH$_3$); 3.64 (s, CH$_3$N), 3.66 (s, CH$_2$); 3.73 (s, COOCH$_3$); 6.5 (s, br. OH). MS: M$^+$=184. IR (KBr): 1731 cm$^{-1}$ (COO).

Example 3

Methyl 4-(4-chlorophenylthio)-3-(2-ethylidene-1-methylhydrazino)-4-oxo-butyrate

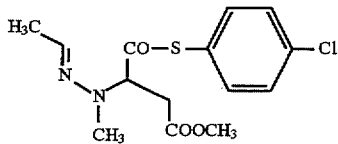

A solution of 8.7 ml of chloroisobutylformate (66.6 mmoles) in 10 ml CHCl$_3$ is added dropwise at –20° C. to a solution of 15 g of methyl 3-carboxy-3-(2-ethylidene-1-methylhydrazino)-propionate triethylamine salt (55.62 mmoles) and 93 ml triethylamine (66.75 mmoles) in 150 ml CHCl$_3$. The mixture is stirred for 1 hour and treated with a solution of 12.06 g of 4-chloro-thiophenol (83.4 mmoles) in 20 ml CHCl$_3$ at –20° C. After stirring for 30 min. at –20° C. and for 2 hours at 20° C. the reaction mixture is washed with water. The organic phase is dried with Na$_2$SO$_4$ and evaporated. The oily residue is purified by chromatography on silica gel. Eluent: toluene/ethyl acetate 9:1. Yield: 11.5 g of methyl 4-(4-chlorophenylthio)-3-(2-ethylidene-1-methyl-hydrazino)-4-oxo-butyrate as a yellowish oil which solidifies on standing (63%). mp: 45°–46° C.

$^1$H-NMR (360 MHz in CDCl$_3$): 1.95 (d, J=6 Hz, CH$_3$CH=); 2.73 (dd, J$_1$=16 Hz, J$_2$=6 Hz, CHHCOO); 2.82 (s, CH$_3$N); 2.93 (dd, J$_1$=16 Hz, J$_2$=6 Hz, CHHCOO); 3.67 (s, COOCH$_3$); 4.59 (t, J=6 Hz; NCHCOO); 6.73 (q, J=6 Hz, CH$_3$CH=); 7.3–7.4 (m, Ph-H). MS: MH$^+$=329/331.

Following the procedure of Example 3, and employing instead of 4-chlorothiophenol one of following phenols or thiophenols:

4-methylthiophenol,
4-methoxy-thiophenol,
4-nitrophenol,
4-cyanophenol,
ethyl 4-hydroxy benzoate,
4-benzoylphenol,
α-naphthol,
β-naphthol,
the following compounds of formula V may be prepared:

methyl 4-(4-methylphenylthio)-3-(2-ethylidene-1-methylhydrazino)-4-oxo-butyrate, mp.: 55°–56° C. $^1$H-NMR (360 MHz in CDCl$_3$): 1.94 (d, J=6 Hz, CH$_3$CH=); 2.37 (s, CH$_3$); 2.74 (dd, J$_1$=16 Hz, J$_2$=6 Hz, CHHCOO); 2.82 (s, CH$_3$N); 2.94 (dd, J$_1$=16 Hz, J$_2$=6 Hz, CHHCOO); 3.68 (s, COOCH$_3$); 4.62 (t, J=6 Hz; NCHCOO); 6.70 (q, J=6 Hz, CH$_3$CH=); 7.15–7.31 (m, Ph-H). MS: MH$^+$=309;

methyl 4-(4-methoxy-phenylthio)-3-(2-ethylidene-1-methylhydrazino)-4-oxo-butyrate, mp.: 53°–55° C. $^1$H-NMR (360 MHz in CDCl$_3$): 1.94 (d, J=6 Hz, CH$_3$CH);; 223 (dd, J$_1$=16 Hz, J$_2$=6 Hz, CHHCOO); 2.82 (s, CH$_3$N); 2.93 (dd, J$_1$=16 Hz, J$_2$=6 Hz, CHHCOO); 3.67 (s, COOCH$_3$); 3.82 (s, CH$_3$O); 4.61 (t, J=6 Hz, NCHCOO); 6.70 (q, J=6 Hz, CH$_3$CH=); 6.90–6.96 (m, Ph-H); 7.27–7.33 (m, Ph-H). MS: MH$^+$=325;

methyl 4-(4-nitro-phenoxy)-3-(2-ethylidene-1-methylhydrazino)-4-oxo-butyrate, mp: 96°–97° C. $^1$H-NMR (360 MHz in CDCl$_3$): 1.92 (d, J=6 Hz, CH$_3$CH=); 2.90 (s, CH$_3$N); 2.97 (dd, J$_1$=16 Hz, J$_2$=6 Hz, CHHCOO); 3.14 (dd, J$_1$=16 Hz, J$_2$=6 Hz, CHHCOO); 3.74 (s, COOCH$_3$); 4.54 (t, J=6 Hz, NCHCOO); 6.74 (q, J=6 Hz, CH$_3$CH=); 7.23–7.30 (m, Ph-H); 8.23–8.30 (m, Ph-H). MS: MH$^+$=324;

methyl 4-(4-cyanophenyloxy)-3-(2-ethylidene-1-methylhydrazino)-4-oxo-butyrate, mp.: 53°–54° C. $^1$H-NMR, (200 MHz in CDCl$_3$): 1.92 (d, J=6 Hz, CH$_3$CH=); 2.88 (s, CH$_3$N); 2.96 (dd, J$_1$=16 Hz, J$_2$=6 Hz, CHHCOO); 3.14 (dd, J$_1$=16 Hz, J$_2$=6 Hz, CHHCOO); 3.72 (s, COOCH$_3$); 4.51 (t, J=6 Hz, NCHCOO); 6.72 (q, J=6 Hz, CH$_2$CH=); 7.20 (d, J=10 Hz, Ph-H); 7.67 (d, J=10 Hz, Ph-H). GC-MS: M$^+$3093;

methyl 4-(4-ethoxycarbonylphenoxy)-3-(2-ethylidene-1-methylhydrazino)-4-oxo-butyrate, mp.: 62°–64° C. $^1$H-NMR (200 MHz in CDCl$_3$): 1.38 (t, J=7 Hz, CH$_3$CH$_2$O); 1.92 (d, J=6 Hz, CH$_3$CH=); 2.89 (s, CH$_3$N); 2.98 (dd, J$_1$=16 Hz, J$_2$=6 Hz, CHHCOO); 3.15 (dd, J$_1$=16 Hz, J$_2$=6 Hz, CHHCOO); 3.73 (s, COOCH$_3$); 4.37 (q, J=7 Hz, CH$_2$O); 4.52 (t, J=6 Hz; NCHCOO); 6.72 (q, J=6 Hz, CH$_3$CH=); 7.12 (d, J=10 Hz, Ph-H); 8.05 (d, J=10 Hz, Ph-H). GC-MS: M$^+$=350;

methyl 4-(4-benzoylphenoxy)-3-(2-ethylidene-1-methylhydrazino)-4-oxo-butyrate, mp.: 59°–60° C. $^1$H-NMR (360 MHz in CDCl$_3$): 1.93 (d, J=6 Hz, CH$_3$CH=); 2.90 (s, CH$_3$N); 3.00 (dd, J$_1$=16 Hz, J$_2$=6 Hz, CHHCOO); 3.16 (dd, J$_1$=16 Hz, J$_2$6 Hz, CHHCOO); 3.74 (s, COOCH$_3$); 4.56 (t, J=6 Hz, NCHCOO); 6.74 (q, J=6 Hz, CH$_3$CH=); 7.15–7.87 (m, Ph-H). GC-MS: M$^+$=382;

methyl 4-(1-naphthyloxy)-3-(2-ethylidene-1-methylhydrazino)-4-oxo-butyrate, reddish oil. $^1$H-NMR (360 MHz in CDCl$_3$): 2.01 (d, J=6 Hz, CH$_3$CH=); 2.97 (s, CH$_3$N); 3.07 (dd, J$_1$=16 Hz, J$_2$=6 Hz, CHHCOO); 3.27 (dd, J$_1$=16 Hz, J$_2$=6 Hz, CHHCOO); 3.74 (s, COOCH$_3$); 4.70 (t, J=6 Hz; NCHCOO); 6.79 (q, J=6 Hz, CH$_3$CH=); 7.17–8.0 (m, Ph-H). GC-MS: M$^+$=328;

methyl 4-(2-naphthyloxy)-3-(2-ethylidene-1-methylhydrazino)-4-oxo-butyrate, mp.: 60°–61° C. $^1$H-NMR (360 MHz in CDCl$_3$): 1.95 (d, J=6 Hz, CH$_3$CH=); 2.93 (s, CH$_3$N); 3.03 (dd, J$_1$=16 Hz, J$_2$=6 Hz, CHHCOO); 3.19 (dd, J$_1$=16 Hz, J$_2$=6 Hz, CHHCOO); 3.74 (s, COOCH$_3$); 4.60 (t, J=6 Hz; NCHCOO); 6.76 (q, J=6 Hz, CH$_3$CH=); 7.17–7.86 (m, Ph-H). GC-MS: M$^{30}$=328.

Example 4

Methyl 3-carboxy-3-(2-ethylidene-1-methylhydrazino)-propionate triethylamine salt

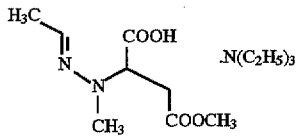

a) Maleic acid monomethyl ester

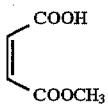

225 g maleic anhydride are added slowly at +60° C. to 1500 ml of methanol. The mixture is stirred for 2 hours at α60° C. and evaporated completely. Yield: 294.3 g of maleic acid monomethyl ester as colorless oily residue (99%).

$^1$H-NMR (360 MHz in CHCl$_3$): 3.90 (s, COOCH$_3$); 6.40 (d, J=12 Hz, CH=); 6.45 (d, J=12 Hz; CH=).

b) A solution of 88.5 g methylhydrazine (1.92 moles) in 340 ml THF is added at +25° C. to a solution of 250 g maleic acid monomethyl ester (1.92 moles) and 194.5 g triethylamine (1.92 moles) in 1850 ml THF. During the addition a precipitation of the triethylamine salt of the intermediate methyl 3-carboxy-3-(1-methyl-hydrazino)-propionate is formed. After stirring for 2 hours at +25° C., a solution of 101.6 g acetaldehyde (2.3 moles) in 370 ml THF is added at +25° C. The precipitation dissolves during the addition. After stirring for 1 hour at +25° C. the solution is evaporated completely. To remove traces of water or methanol, the residue is mixed with 750 ml toluene and evaporated again completely (10 mbar, 60° C.). Yield: 429.6 g of methyl 3-carboxy-3-(2-ethylidene-1-methylhydrazine)-propionate triethylamine salt as viscous yellow oil (83%).

$^1$H-NMR (360 MHz in CHCl$_3$): 1.25 (t, J=7 Hz; CH$_3$—CH$_2$N); 1.88 (d, J=6 Hz, CH$_3$CH=); 2.70–2.80 (m, CHHCOO); 2.77 (s, CH$_3$N); 2.95 (dd, J$_1$=16 Hz, J$_2$=6 Hz, CHHCOO); 3.03 (q, J=7 Hz, NCH$_2$CH$_3$); 3.67 (s, COOCH$_3$); 4.32 (t, J=6 Hz; NCHCOO); 6.63 (q, J=6 Hz, CH$_3$CH=).

Example 5

Methyl α-[1,3-dimethyl-4-(2,5-dichlorobenzyloxy)-1H-pyrazol-5-yl]-α-methoximino acetate

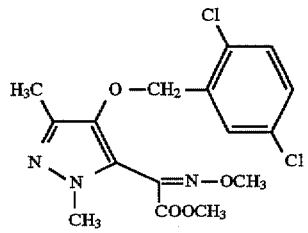

Methyl α-[1,3-dimethyl-4-(2,5-dichlorobenzyloxy)-1H-pyrazol-5-yl]acetate (10 g, 29 mmol) is added in one portion to a solution of potassium tert. butylate (5.6 g, 50 mmol) in 1,2-dimethoxyethane (80 ml) at −40° C. After 30 minutes tert. butylnitrite (15 ml) is added and the mixture is stirred at room temperature for 30 minutes. Dimethyl sulfate (6.3 g, 50 mmol) is added with cooling. After 4 hours the mixture is diluted with ether, washed with brine and dried over MgSO$_4$. Evaporation of the solvent and chromatography on silicagel (eluant: hexane/ethyl acetate, 10:1) gives the E- and Z-isomers of methyl α[1,3-dimethyl-4-(2,5-dichlorobenzyloxy)-1H-pyrazol-5-yl]-α-methoximino acetate in form of crystalline solids, m.p. 81° C. (E) and 90° C. (Z).

Example 6

N-methyl α-[1,3-dimethyl-4-(2,5-dichlorobenzyloxy)-1H-pyrazol-5-yl]-α-methoximino acetamide

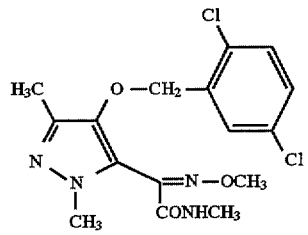

Methyl α-[1,3-dimethyl-4-(2,5-dichlorobenzyloxy)-1H-pyrazol-5-yl]-α-methoximino acetate (2.1 g, 5.3 mmol) is dissolved in 20 ml of DMF in which 1.3 ml, 40% of methylamine has been solved before. After stirring for 90 min the reaction is completed and the reaction mixtures poured into water, extracted with ethyl acetate (3.50 ml) and washed with brine. The organic layer dried over Na$_2$SO$_4$, filtered and concentrated. Purification by column chromatography on silica gel gives the E and Z isomers of N-methyl α-[1,3-dimethyl-4-(2,5-dichlorobenzyloxy)-1H-pyrazol-5-yl]-α-methoximino acetamide in form of crystalline solids; m.p. 91° C. (E) and 158° C. (Z).

What is claimed is:

1. Process for the preparation of a 4-hydroxypyrazole of formula III

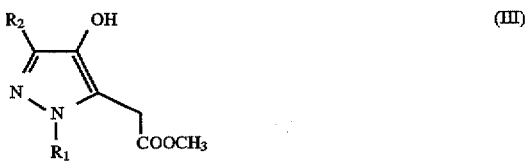

(III)

wherein R$_1$ is C$_{1-5}$alkyl and R$_2$ is hydrogen or C$_{1-5}$alkyl, comprising an intramolecular cyclization reaction of a compound of formula V

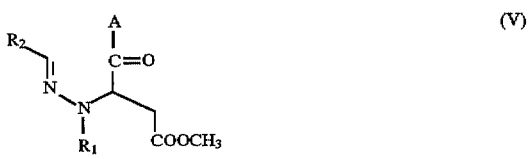

(V)

wherein R$_1$ and R$_2$ are as defined for formula III, and A is a leaving group, at a temperature between +50° C. and +200° C.

* * * * *

UNITED STATES PATENT AND TRADEMARK OFFICE
CERTIFICATE OF CORRECTION

PATENT NO. : 5,670,648
DATED : Sept. 23, 1997
INVENTOR(S) : E. Waldvogel et al.

It is certified that error appears in the above-identified patent and that said Letters Patent is hereby corrected as shown below:

On the title page: Item [30] foreign priority is claimed to Great Britain, 9417971, filed Sept. 7, 1994.

Signed and Sealed this

Fifth Day of January, 1999

Attest:

*Attesting Officer*

*Acting Commissioner of Patents and Trademarks*